(12) United States Patent
Myung (10) Patent No.: US 10,893,961 B2
(45) Date of Patent: Jan. 19, 2021

(54) METHOD OF MANUFACTURING MEDICAL STENT WITH REINFORCED SUPPORTIVE RIM (71) Applicant: BCM Co., Ltd., Gyeonggi-do (KR)

(72) Inventor: Byung Cheol Myung, Gyeonggi-do (KR)

(73) Assignee: BCM Co., Ltd., Gyeonggi-do (KR)

( * ) Notice: Subject to any disclaimer, the term of this patent is extended or adjusted under 35 U.S.C. 154(b) by 0 days.

(21) Appl. No.: 16/099,146

(22) PCT Filed: Dec. 15, 2016

(86) PCT No.: PCT/KR2016/014697
§ 371 (c)(1),
(2) Date: Nov. 5, 2018

(87) PCT Pub. No.: WO2018/110736
PCT Pub. Date: Jun. 21, 2018

(65) Prior Publication Data
US 2019/0298554 A1 Oct. 3, 2019

(51) Int. Cl.
A61F 2/90 (2013.01)
A61B 17/11 (2006.01)
A61F 2/89 (2013.01)
A61F 2/82 (2013.01)

(52) U.S. Cl.
CPC ............... *A61F 2/90* (2013.01); *A61B 17/11* (2013.01); *A61F 2/82* (2013.01); *A61F 2/89* (2013.01)

(58) Field of Classification Search
CPC ...... A61F 2/90; A61F 2/82; A61F 2/89; A61F 2/2415; A61F 2230/0078; A61F 2230/0065; A61B 17/11
See application file for complete search history.

(56) References Cited

U.S. PATENT DOCUMENTS

| 6,620,122 B2 | 9/2003 | Stinson et al. |
| 8,454,632 B2 | 6/2013 | Binmoeller et al. |
| 2010/0241218 A1 | 9/2010 | Bruszewski et al. |

FOREIGN PATENT DOCUMENTS

| KR | 1020110002389 | 1/2011 |
| KR | 1020130005519 | 1/2013 |
| KR | 1020140094144 | 7/2014 |
| KR | 101691118 | 12/2016 |

*Primary Examiner* — Moshe Wilensky
(74) *Attorney, Agent, or Firm* — IP & T Group LLP (57) ABSTRACT A medical stent for use in a procedure for connecting two adjacent tissues in a human organ to form a passageway therebetween or a procedure for draining or shunting away internal fluids such as bile, pus, or the like. To manufacture the stent, a hollow tubular mesh body having diamond-like cells is weaved using super-elastic shape memory wire strands, both axial ends of the mesh body are expanded and multi-folded to form washer-shaped ends, and the both washer-shaped ends are provided with respective reinforced supportive rims formed by narrowing the cells of the end portions of the mesh body such that the wire strands at each axial end of the mesh body are superimposed to improve radial supporting force. The stent can lock in place when staying implanted in a human body.

12 Claims, 7 Drawing Sheets

METHOD OF MANUFACTURING MEDICAL STENT WITH REINFORCED SUPPORTIVE RIM

This application is a national stage application of PCT/KR2016/014697 filed on Dec. 15, 2016. The disclosure of each of the foregoing applications is incorporated herein by reference in its entirety.

TECHNICAL FIELD

The present invention relates to a method of manufacturing a medical stent for a procedure for puncturing and connecting two adjacent tissues in an internal organ such as gall bladder, pancreas, etc., to secure a passageway between the tissues or for a procedure for drainage or shunting of bile, pus, or the like, and relates to a medical stent produced through the manufacturing method. More particularly, the present invention relates to a method of manufacturing a medical stent with reinforced supportive rims, the method including: weaving a hollow tubular mesh body having diamond-like cells by crossing super-elastic shape-memory alloy wire strands; expanding in a radial direction and compressing in an axial direction each axial end portion of the hollow tubular mesh body to form washer-shaped ends at the respective axial ends of the hollow tubular mesh body such that each washer-shaped end is provided with a reinforced supportive rim at the circumferential periphery of the hollow tubular mesh body, in which the reinforced supportive rim is formed by extremely narrowing the cells formed at the axial end of the hollow tubular mesh body and by superimposing or stacking the ends of the wire strands on each other, whereby the resistance of the axial end of the medical stent against an external force applied thereto is increased, which enables human tissues connected by the medical stent to be maintained in a securely connected state for a long term. The present invention also relates to a medical stent with a reinforced supportive rim produced through the same manufacturing method.

BACKGROUND ART

In medicine, a stent is widely used in an interventional procedure to recover smooth flow of a fluid, for example, blood, food, or internal fluids through a lumen when migrate suffers stenosis which is likely to occur due to arteriosclerosis, thrombosis, benign malignant tumor, postoperative complications, or pathological causes. Stenting has been in use since the 1980s and is an important procedure since then.

Stents are largely divided into non-vascular and vascular stents. Nowadays, well-known are self-expanding stents which have a metal or polymer mesh structure having elasticity, thereby contracting when external force is applied thereto and expanding to their original shape when the external force is removed.

The stent-based procedures are broadly classified into vascular stenting and non-vascular stenting.

The former vascular stenting is known as a procedure which is performed such that an opening of 3 mm to 4 mm is made in the thigh, then a thin tube called "catheter" is advanced to a lesion site through the femoral artery, and a stent is inserted through the internal channel of the catheter to expand the narrowed blood vessel.

The latter non-vascular stenting known to be mainly performed when the occlusion of the esophagus occurs or is in progress due to an esophageal cancer. That is, when the esophagus is clogged by cancerous tissue or the like, the ingestion of food from the mouth becomes impossible. In this case, a balloon catheter is placed in the esophagus and the balloon is inflated to dilate the stenosis for securing a food intake passage.

For the above-described procedures, there has been an effort to improve the functions of stents, so that various structures of stents have been suggested and disclosed to achieve the purpose.

In the case of stents that are not for special purposes, they are usually manufactured in a manner of crossing super-elastic shape-memory alloy wire or stainless-steel wire over and under each other, or in a manner of engaging peak and valley parts of sinusoid wires to form a hollow tubular mesh body having a plurality of rhombic openings (cells) and a predetermined length.

On the other hand, recently, connection stents have been used to enable for a doctor to access an internal organ, such as the gallbladder or the pancreas which it is difficult to directly conduct an endoscopic treatment thereon or to conduct an operation of draining or shunting away a fluid, such as bile, pus, or the like.

That is, after piercing adjacent tissues of an organ, such as gall bladder, pancreas, etc., a stent is inserted through the pierced holes so that the tissues can communicate with each other through a passageway provided in the stent.

Regarding a stent, a conventional art is disclosed in U.S. Pat. No. 6,620,122. According to the conventional art, a hollow tubular mesh body is weaved by crossing alloy wires, specifically super-elastic shape-memory alloy wires, in an overlapping manner. Then, increased diameter parts are formed at respective ends of the hollow tubular mesh body to produce a dumbbell-shaped mesh stent. The dumbbell-shaped mesh stent may be directly inserted into the tissue of a human internal organ. The diameter-increased parts are anchored to adjacent tissues of the human internal organ so that the stent may not be displaced or removed from the organ. That is, the adjacent tissues of the human internal organ can be securely connected to each other.

Such a conventional technique has a problem in that the stent in some locations will easily slipped out of an implanted site due to an external force applied thereto during normal external body motion and normal motion of internal organs.

In addition, when comparing the size of the openings (cells) of a main body portion of such a conventional stent and the size of the openings (cells) of diameter increased parts provided at both sides of the main body portion, the size of the openings (cells) of the diameter increased parts is larger because the diameter increased parts are formed by expanding both end portions of a tubular body configured to have a uniform diameter. Therefore, is inevitable that the physical strength of the diameter increased parts is weaker than that of the main body portion, which causes a problem such as displacement or slipping of the stent from the placed site.

As another conventional art, U.S. Pat. No. 8,454,632 discloses a technique in which the above-mentioned problems are somewhat improved. A hollow tubular body formed by braiding an alloy wire such as a super-elastic shape-memory alloy wire is inserted through the pierced hole of a human organ, and then both axial end portions of the hollow tubular body are partially pushed inward to be inserted into the lumen of the hollow tubular body so that double wall flanges are formed at the respective axial ends of the hollow tubular body. The double wall flanges are respectively caught by adjacent tissues, which prevents the stent from being easily removed from the placed site in the human body.

This has a disadvantage in that it is not avoidable that the manufacturing process of the stent is complicated because the double wall flanges on both sides of the tubular body needs to be formed to have a larger diameter than that of the middle portion of the tubular body.

That is, since the stent is produced by crossing alloy wires over and under, the stent can elongate in the axial direction. However, it is impossible to stretch the interwoven body without any constraints. That is, the elongation is allowed only within the deformable range of the rhombic cells.

Therefore, there is a disadvantage that the complicated manufacturing process is required in which in order to form the double wall flanges on both sides of the tubular body, the both end portions of the tubular body need to be woven first in a relatively large diameter, and then thermosetting for shape memory needs to be performed so that the superimposed walls at the respective end portions of the tubular body come into tight contact with each other.

In addition, there is a problem in that the stenting procedure is complex and can be performed only by a skilled operator because the procedure operator needs to form and maintain the double wall flanges by himself or herself by carefully pulling or pushing the both end portions of the tubular body with an elastic bar or the like while the tubular body is disposed inside the human body.

For these reasons, according to the conventional techniques, it was difficult to place and lock a stent to adjacent tissues such that the adjacent tissues are in tight elastic contact with each other, and thus there was a problem that it was difficult to drain or shunt away an internal fluid such as bile, pus, or the like due to the occurrence of a gap between the adjacent tissues. Furthermore, there was a problem of a high probability that the stent slips out of the placed site to be displaced when the patient moves.

DISCLOSURE

Technical Problem

The present invention has been made to solve the problems of the conventional arts described above, and it is intended to solve the following problems.

The present invention is intended to provide a method of manufacturing a medical stent with a reinforced supportive rim, in which the reinforced supportive rim made from a stent material is integrally formed at an axial end of a stent which to penetrate through two adjacent tissue layers for connection of the tissue layers so that the stent may securely lock in place not be displaced from a position at which the stent as placed. The present invention also provides a medical stent with a reinforced supportive rim produced through the same manufacturing method.

The present invention is intended to provide a method of manufacturing a medical stent with a reinforced supportive rim, in which the reinforced supportive rim is formed by expanding and folding an axial end portion of a tubular mesh body having a uniform diameter. Since a tubular mesh body having a uniform diameter over the entire length thereof is used to manufacture the stent according to the present invention, the manufacturing method of the stent can be simplified. The present invention also provides a medical stent with a reinforced supportive rim produced through the same manufacturing method.

The present invention is intended to provide a method of manufacturing a medical stent with a reinforced supportive rim which facilitates a stent-directed procedure. That is, a doctor or operator only needs to insert a catheter into the medical stent of the present invention in an operating room, to expand a washer-shaped end of the medical stent, which increases a securable locking area of the medical stent in the tissue layers of a patient. The present invention also provides a medical stent produced through the manufacturing method.

The present invention is intended to provide a medical stent with a reinforced supportive rim having a multi-folded configuration, in which the deformation resistance of the supportive rim can be adjusted by changing a width of an axial peripheral portion of a tubular mesh body, which to convert into a washer-shaped, i.e., by changing the number of folds in the multi-folded configuration formed by folding and compressing the axial peripheral portion of the tubular mesh body. Therefore, the present invention can provide a medical stent with a reinforced supportive rim having a desired resistance by using the same manufacturing method.

Technical Solution

In order to accomplish the above objectives, the present invention provides a method of manufacturing a medical stent with a reinforced supportive rim, and a medical stent produced through the same manufacturing method. In the method, both axial end portions of a uniform-diameter tubular mesh body to become a stent which to penetrate through two adjacent tissue layers of an organ for connection of the tissue layers, are expanded into washer configurations, and each of the washer-shaped end of the tubular mesh body is provided with a reinforced supportive rim having a multi-folded configuration to exhibit super-elasticity at a circumferential periphery thereof. The present invention also provides a medical stent with a reinforced supportive rim, produced through the same manufacturing method.

According to the present invention, the number of folds (turns) of the supportive rim provided at the circumferential periphery of the washer-shaped end of the tubular mesh body to impart a high bearing capacity based on high elasticity may be adjustable.

According to the present invention, since the stent has washer-shaped ends of a tubular mesh body serving as a principal body portion of a stent and a reinforced supportive rim along a circumferential periphery of the washer-shaped end, the stent can be strongly locked in place due to the washer-shaped ends and can provide strong radial force to resist against an external force due to the reinforced supportive rim.

Advantageous Effects

As described above, according to the present invention, since the reinforced supportive rims made of the same material as the stent are integrally formed at the respective axial ends of the stent that supports two adjacent lumen tissue layers, the stent may securely lock in place so that it may not be displaced from a target position. Furthermore, since the washer-shaped end portion is formed by folding and erecting the end portion of the tubular mesh body having a uniform diameter, the method of manufacturing the stent is very easy and simple. Furthermore, since the washer-shaped end of the stent expands in an easy way whereby a doctor or operator simply inserts an existing catheter into the stent in an operating room and the washer-shaped end of the stent is configured to provide a sufficient locking area such that the stent can be securely anchored in to two adjacent lumen tissue layers, a stenting procedure becomes easy and simple by using the stent of the invention. Furthermore, since the degree of overlapping (the number of folds or turns) in the reinforced supportive rims is adjustable by adjusting the width of a peripheral portion of the tubular mesh body, which to form the washer-shaped end, the end resistance of the stent can be adjusted as desired. That is, the present invention has various effects. For example, it is possible to manufacture a stent that can securely support the internal wall of a body cavity because it has strong resistance against the radial force in a state of being placed, there is little likelihood that the deformation of the tip of the stent occurs.

BEST MODE

Hereinafter, a method of manufacturing a stent, according to the present invention, will be described with reference to the accompanying drawings.

Figure 1:
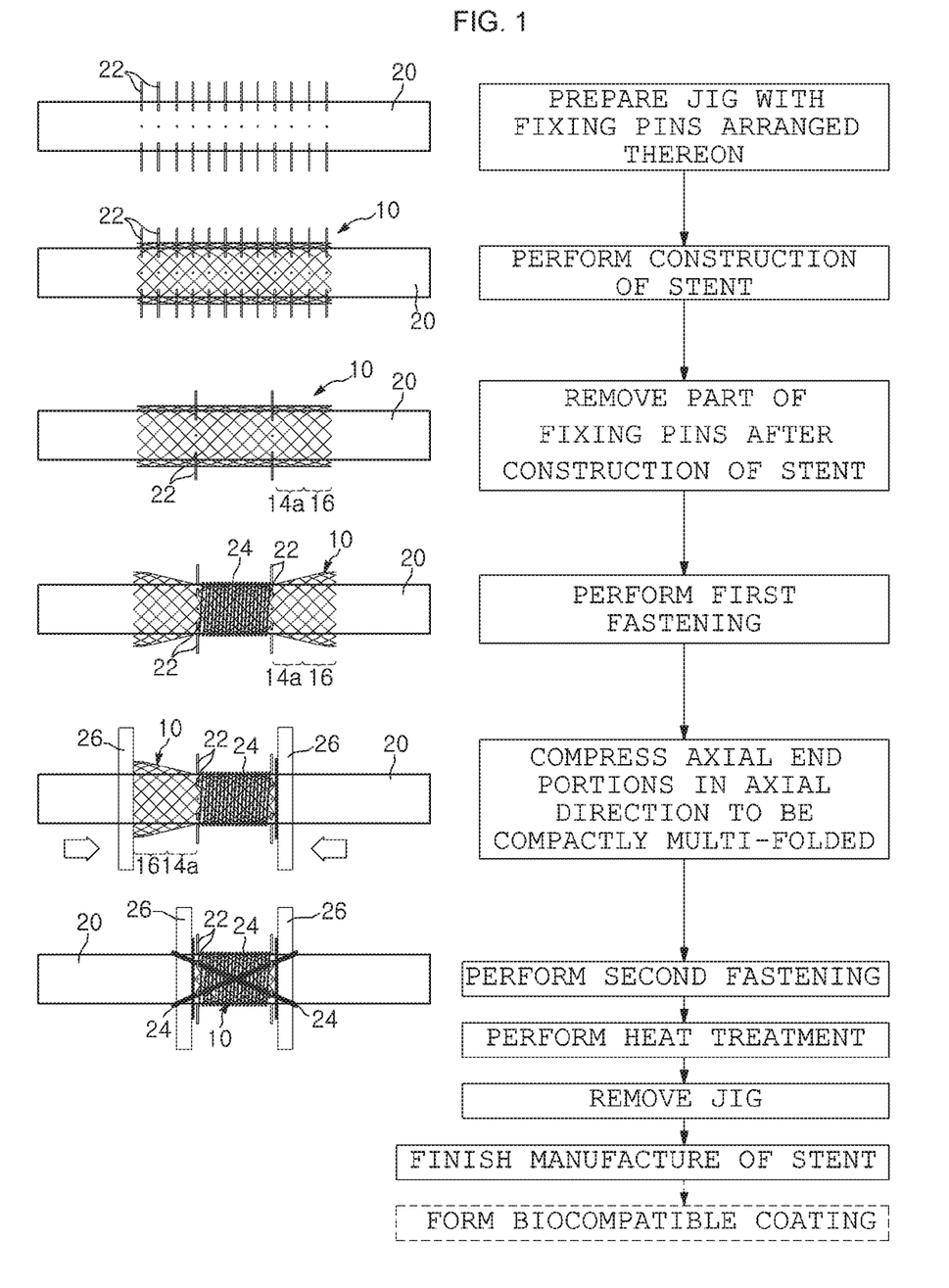
FIG. 1 is a flowchart illustrating a method of manufacturing a medical stent according to a first embodiment of the present invention.
Figure 2:
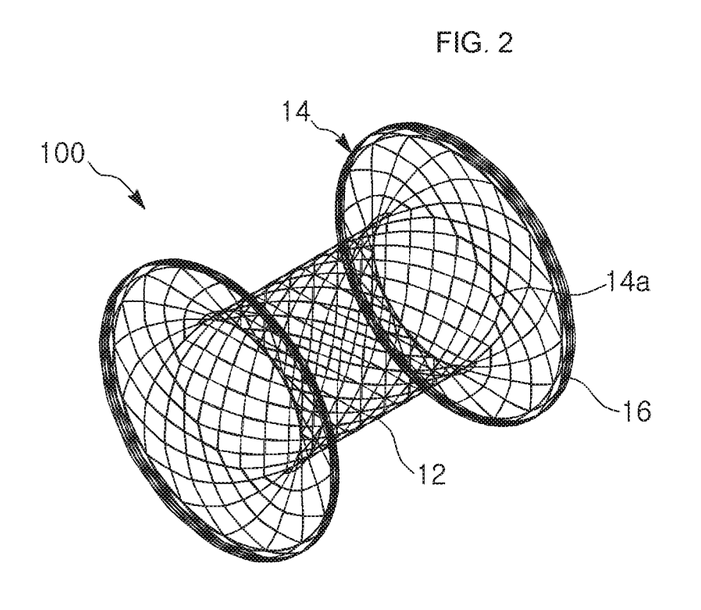
FIG. 2 is a perspective view illustrating the appearance of a medical stent manufactured through the manufacturing method illustrated in FIG. 1.

The method of manufacturing a stent, according to the present invention, will be described with reference to a basic embodiment (also referred to as a first embodiment) of the present invention illustrated in FIGS. 1 and 2.

The method includes: a jig preparation step of preparing a jig on which fixing pins are arranged, the jig being used to construct a tubular mesh body 12 for a stent by crossing over and under stent material wires to manufacture the stent;

a stent construction step of weaving the tubular mesh body 12 from a first wire strand such that the tubular mesh body 12 is fitted over a surface of the jig;

a fixing pin removal step of removing all of the fixing pins from the jig except for some fixing pins positioned in such a manner to demarcate an area of the tubular mesh body 12, which to become a principal body portion of a stent later, among the fixing pins arranged on the jig;

a first fastening step of fastening the principal body portion of the tubular mesh body 12 to the surface of the jig by winding a second wire strand 24 around the principal body portion of the tubular mesh body 12 fitted on the surface of the jig, while leaving both axial periphery portions of the tubular mesh body 12 unwound by the second wire strand 24, in which each of the unwound periphery portion has a predetermined width L;

a compression step of compressing, toward an axial middle portion of the tubular mesh body 12, the peripheral portions of the tubular mesh body 12, each of which is expanded in an inwardly tapered form when the second wire strand 24 is wound around the principal body portion of the tubular mesh body such that the principal body portion of the tubular mesh body is tightly fastened to the surface of the jig 20, by pushing respective outer ends of the peripheral portions, from opposing directions, toward the axial middle portion of the tubular mesh body 12, with respective disks 26 disposed in direct surface contact with the outer ends of the peripheral portions of the tubular mesh body 12;

a second fastening step of fastening the disks 26 to the outer ends of the tubular mesh body 12 after the peripheral portions of the tubular mesh body are compressed in an axial direction to form a multi-fold configuration until axial movements of the disks 26 are stopped by the remaining fixing pins 22;

a heat treatment step of subjecting the tubular mesh body resulting from the second fastening step to heat treatment for shape memory so that the deformed state of the tubular mesh body is maintained; and a jig removal step of removing the jig from the heat-treated structure to produce a stent 100.

Figure 3:
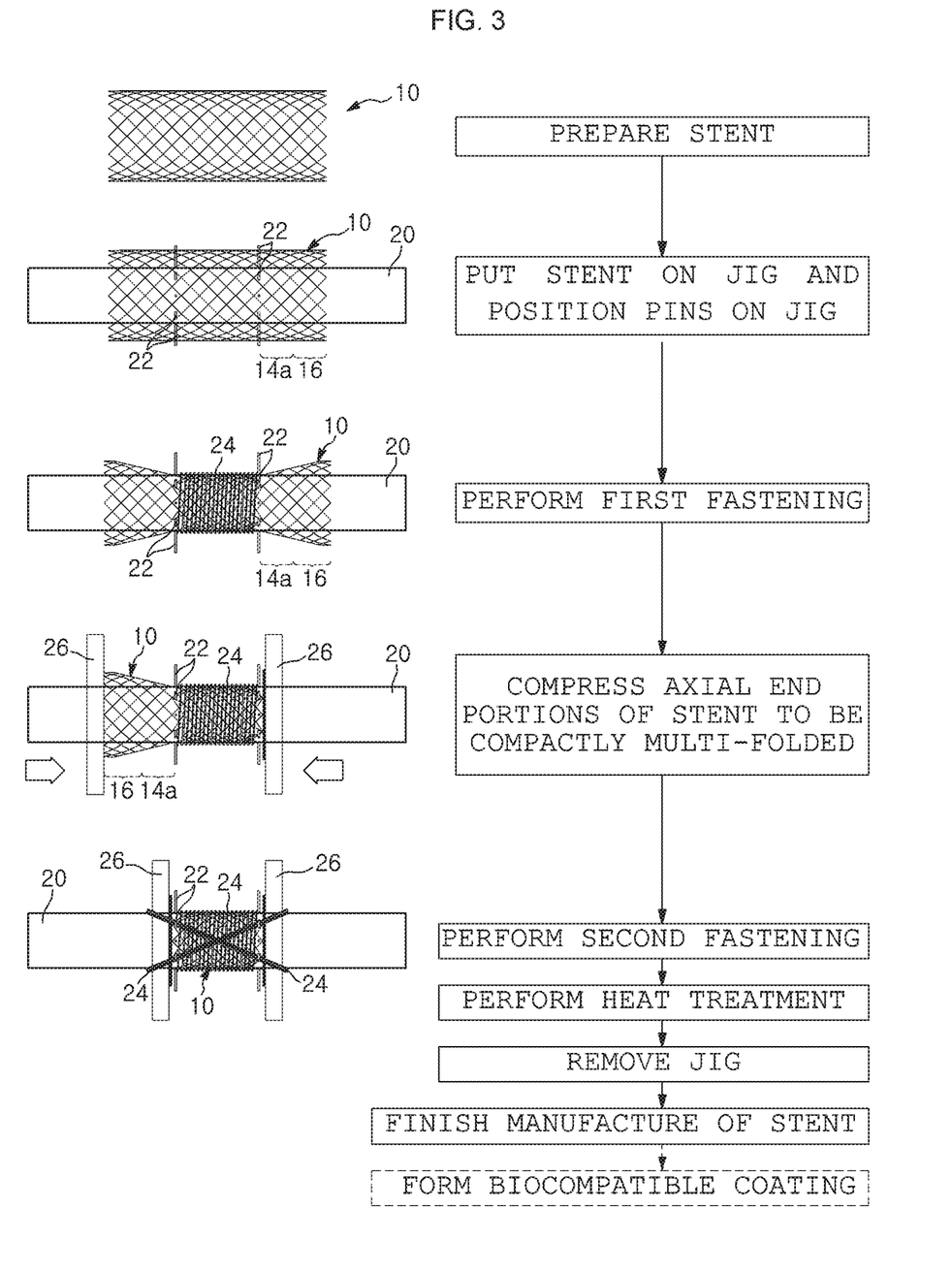
FIG. 3 is a flowchart illustrating a method of manufacturing a medical stent according to a second embodiment of the present invention.

In the manufacturing method according to the first embodiment, all the processes from the weaving step to the jig removal step at which the stent with reinforced supportive rims at respective ends thereof is produced are performed continuously. A stent manufacturing method according to a second embodiment of the present invention, which is described below, differs from that of the first embodiment in that an existing stent is retrofitted to have reinforced supportive rims at respective ends thereof instead of constructing a new stent.

That is, the stent manufacturing method according to the second embodiment, as illustrated in the drawings, includes: a stent preparation step of obtaining (for example, purchasing) a stent 10 having a uniform diameter;

a jig and pin installation step of fitting the stent 10 corresponding to the tubular mesh body 12 in the first embodiment such that a jig 20 having a smaller diameter than the stent 10 is disposed to extend through the lumen of the stent 10 and of arranging a plurality of fixing pins to the jig 20 along a circumferential direction such that the pins are arranged to demarcate a principal body portion of the tubular mesh body 12;

a first fastening step of securely fastening the principal body portion of the tubular mesh body 12 to a surface of the jig 20 by winding a second wire strand 24 around the principal body portion, whereby peripheral portions of the tubular mesh body 12 in a longitudinal direction are expanded into an inwardly tapered form;

a stent compression step of compressing, toward a axial middle portion of the tubular mesh body 12, the peripheral portions of the tubular mesh body 12, each of which is expanded into an inwardly tapered form when the second wire strand 24 is wound around the principal body portion such that the principal body portion of the tubular mesh body can be tightly fastened to the surface of the jig 20, by pushing respective outer ends of the peripheral portions, from opposing directions, toward the axial middle portion of the tubular mesh body 12, with respective disks 26 disposed in direct surface contact with the outer ends of the peripheral portions of the tubular mesh body 12;

a second fastening step of fastening the respective disks 26 to the respective outer ends of the tubular mesh body 12 after the peripheral portions of the tubular mesh body 12 are compressed until axial movements of the disks 26 are stopped by the remaining fixing pins 22;

a heat treatment step of subjecting the tubular mesh body resulting from the second fastening step to heat treatment for shape memory so that the deformed state (compressed state) of the tubular mesh body is maintained; and a jig removal step of removing the jig from the heat-treated structure to produce a stent 100.

Figure 4:
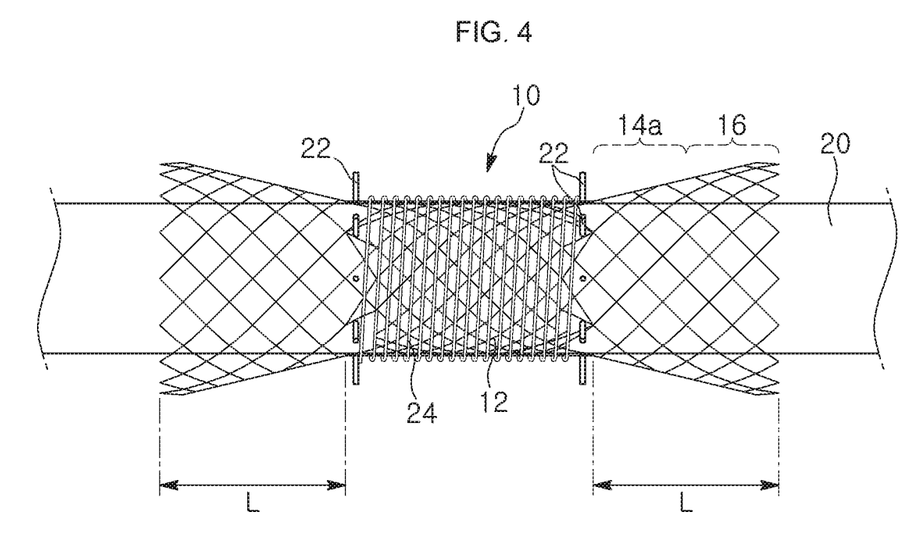
FIG. 4 is a flowchart illustrating a process of deploying a stent, which is included in the manufacturing method of the present invention.
Figure 5:
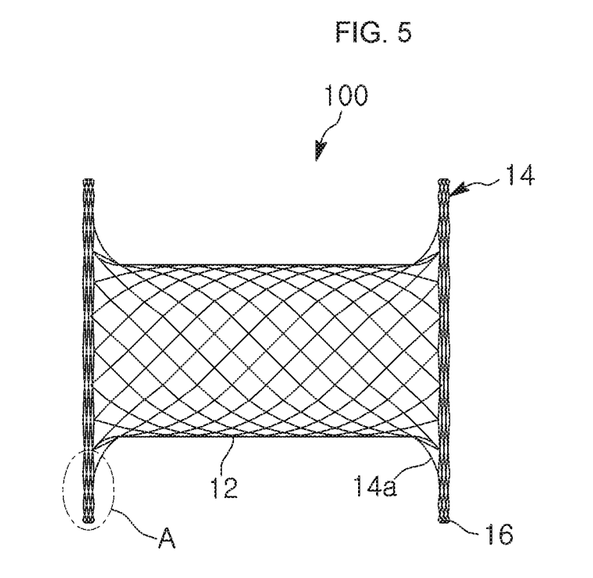
FIG. 5 is a perspective view illustrating the appearance of a stent produced through the manufacturing method of the present invention.
Figure 6:
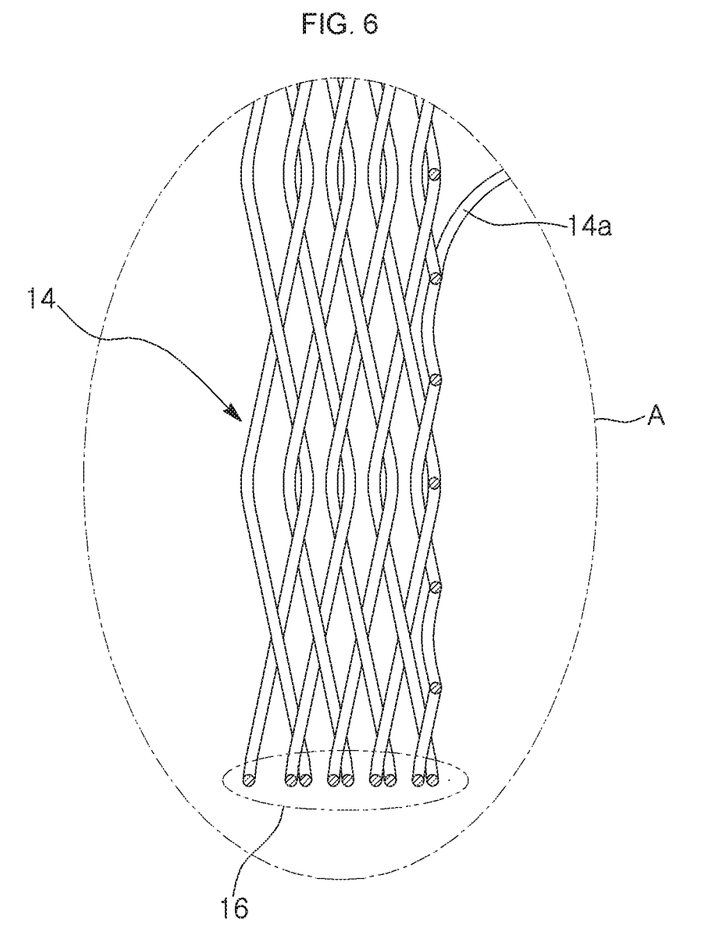
FIG. 6 is an enlarged view illustrating a main portion of a reinforced supportive rim, i.e., an "A" portion of FIG. 5.

When the disks 26 are pushed toward the axial middle portion of the tubular mesh body 12 from opposite directions until the axial direction movements of the disks 26 are stopped by the remaining fixing pins 22 such that the peripheral portions of the tubular mesh body 12 are compressed, the peripheral portions of the stent are expanded in a radial direction and compressed (i.e., folded multiple times into a multi-fold structure) in the axial direction, thereby forming washer-shaped ends 14. At this time, except for boundary portions between the washer-shaped ends 14 and the principal body portion, the peripheral portions of the tubular mesh body, which are expanded in the radial direction to have the maximal diameter, are folded multiple times and superimposed to form a multi-fold structure to form reinforced supportive rims 16 on outer circumferential peripheries of the washer-shaped ends 14, respectively.

Although the second embodiment discloses a structure in which the principal body portion of the tubular mesh body 12 and the washer-shaped ends 14 have the right angle therebetween, they may have an acute angle or an obtuse angle therebetween through a shape memory process. In the case of shaping the stent such that the washer-shaped rims 14 and the principal body portion of the tubular mesh body 12 have an acute angle or an obtuse angle therebetween, such a shape can be obtained by adjusting mounting angles of the disks 26 when the disks 26 are mounted to the jig 20.

The number of folds (also referred to as layers or turns) of the reinforced supportive rim 16 depends on the width L of the peripheral portion of the tubular mesh body 12, which to become the washer-shaped end. That is, the radially resisting force at the axial ends of the stent may vary according to the width of the peripheral portions.

When the width L of the peripheral portion is relatively small, elasticity of the reinforced supportive rim 16 provided at the circumferential periphery of the axial end of the stent is small. That is, the elasticity of the reinforced supportive rim 16 increases as the width L of the peripheral portion which to turn into the reinforced supportive rim 16 is increased.

The manufacturing method according to the present invention may further include a coating step of coating the surface of the resulting stent 100 with an artificial biocompatible coating.

The coating may be formed from PETT that is an excellent biocompatible material, or a silicone film. The types of the coating films that can be provided on the surface of stents are well known in the art.

In describing the first embodiment and the second embodiment of the inventive manufacturing method, the jigs 20, the fixing pins 22, and the finished stents 100 employed in the first and second embodiments are denoted by same reference numerals because those in the first embodiment and the second embodiment are substantially the same between the first embodiment and the second embodiment.

The stent 100 with the reinforced supportive rims produced through the manufacturing method according to the present invention described above will be detailed further below.

As illustrated in FIGS. 5 to 8, the stent according to the present invention includes: washer-shaped ends 14 that are formed by outwardly expanding and folding axial end portions of a tubular mesh body 12 and compressing the axial end portions of the tubular mesh body 12 in an axial direction; and reinforced supportive rims 16 provided at circumferential peripheries of the washer-shaped ends 14, respectively. The reinforced supportive rims 16 increase a tip resistance of the stent against a radial external force applied to the stent.

Figure 7A:
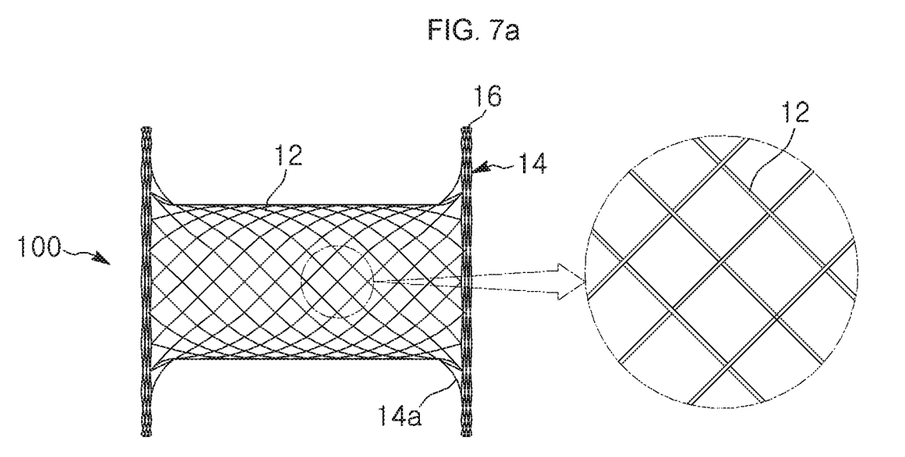
FIGS. 7A and 7B are perspective views illustrating various exemplary stents according to the present invention.
Figure 7B:
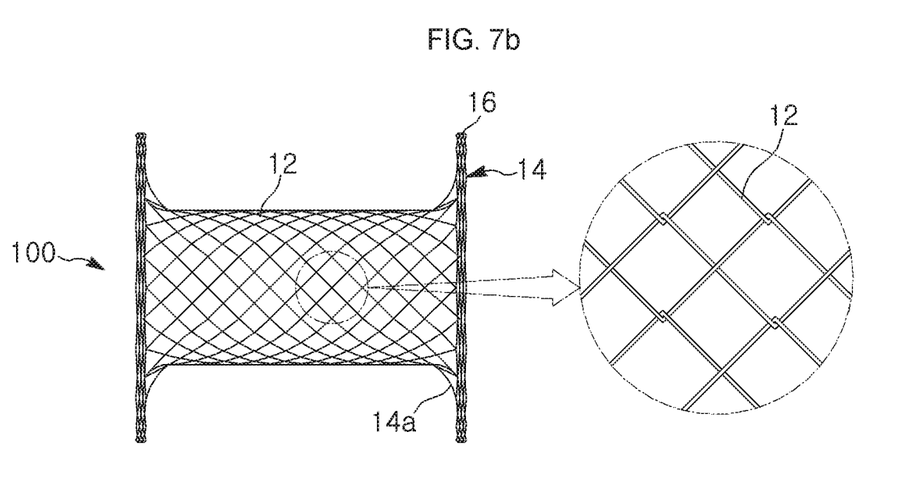

That is, as illustrated in FIG. 7, since each of the washer-shaped ends 14 includes a supporting surface 14a extending from the tubular mesh body 12, a removal preventing structure is formed which prevents the stent from being caught by a tissue and from being removed from a surgical instrument. In addition, the reinforced supportive rims 16 provided at the circumferential peripheries of the washer-shaped ends 14 and disposed outside the supporting surfaces 14a prevent the stent 100 from being displaced from the placed site by the external force applied to the stent 100 by the tissue layers at the placed site. That is, the reinforced supportive rims 16 has a function of securely locking the stent in position. The stent of the present invention may be of the interwoven mesh type formed by crossing wire strands over and under each other, or of the hooked mesh type in which peak and valley parts of sinusoid wires are engaged to form a plurality of diamond-like openings (cells). That is, the present invention is applicable to any type of stent.

Figure 8:
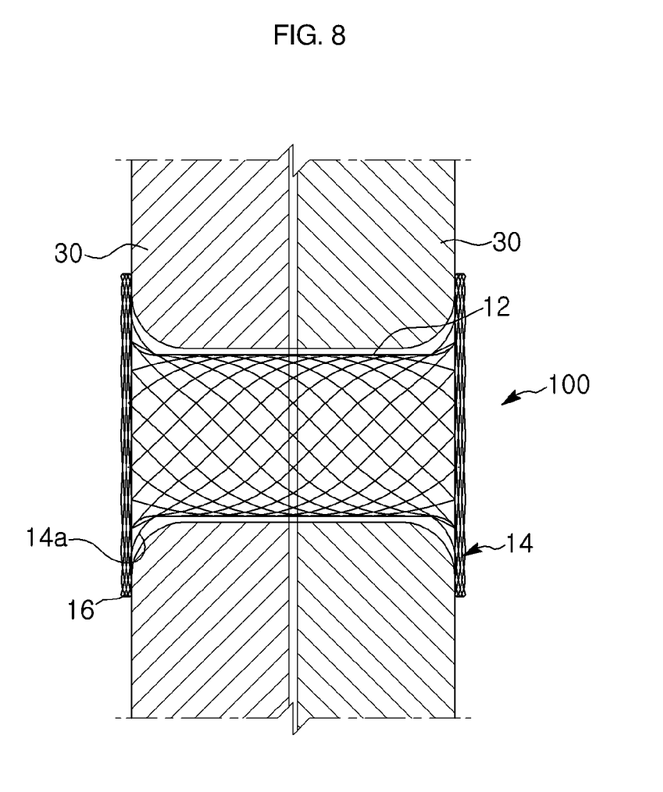
FIG. 8 is a plan view illustrating a state in which the stent of the present invention is placed in a patient body.

As illustrated in FIG. 8, the stent of the present invention described above is used in a procedure in a manner that an existing insertion tool first pierces a human body to form an opening, and the stent is then inserted into the human body through the opening and advanced to a target site while penetrating through two adjacent tissues. When the placement of the stent in the human body is finished, the washer-shaped ends provided at both sides of the central tubular mesh body 12 of the stent 100 are anchored to the tissue layers 30 at the procedure site. Further, due to the presence of the multi-folded reinforced supportive rims 16 on the circumferential peripheries of the washer-shaped ends 14, the resistance of the stent against an external force applied by the tissues and the locking force of the stent in the placed site are dramatically improved.

In the stent 100 according the present invention, the washer-shaped ends 14 having a relatively large diameter compared with the middle portion of the stent are anchored to over a large area of the tissue of the human body. Furthermore, since the multi-folded reinforced supportive rims 16 are provided at the circumferential peripheries of the respective washer-shaped ends 14, contraction deformation of the stent can be suppressed. Still furthermore, since the reinforced supportive rims 16 exhibit strong resistance to an external force applied thereto, deformation of the stent, attributable to an external force, can be prevented.

On the other hand, when withdrawing the sent 100 for removal from the body tissue while holding the stent 100 with an insertion tool, the multi-folded reinforced supportive rims 16 of the stent naturally and smoothly expand into a funnel shape upon coming out of the bored hole in the human body. At this time, contraction pressure can be easily transferred, so that the stent can be extracted while minimizing or preventing damage to the tissue of the human body.

The embodiments that have been described above suggest a structure in which the washer-shaped ends configured to lock the stent in the body tissue at the placed site and the reinforced supportive rims provided at the outer circumferential peripheries of the washer-shaped ends to increase resistance against the external force applied to the stent are provided at both of the axial ends of the stent. However, the present invention is not limited such a structure. That is, only one axial end of a stent may be provided with the washer-shaped end and the reinforced supportive rim. That is, the design of the stent described above can be modified without departing from the gist of the present invention, so that such a modification will be construed to fall within the scope of the present invention.

DESCRIPTION OF THE REFERENCE NUMERALS IN THE DRAWINGS

| | |
|---|---|
| 10, 100: Stent | 12: Cylindrical mesh body |
| 14: Washer-shaped rim | 16: Reinforced supportive rim |
| 20: Jig | 22: Fixing pin |
| 24: Wire | 26: Disk |
| L: Width of peripheral portion in axial direction | |

The invention claimed is:

1. A method of manufacturing a stent with an increased tip resistance, the method forming an expanded part imparting an increased tip resistance to an external force and comprising:
   a preparation step of preparing a jig on which fixing pins are arranged;
   a construction step of constructing a tubular mesh body which to finally form the stent, by weaving the tubular mesh body around the jig with a first wire strand;
   a pin removal step of removing a part of the fixing pins while leaving the remaining part of the fixing pins that are arranged to demarcate a principal body portion of the tubular mesh body;
   a first fastening step of fastening the principal body portion of the tubular mesh body to a surface of the jig by winding a second wire strand around the principle body portion, with axial end portions of the tubular mesh body unwound and uncovered by the second wire strand, each axial end portion having a predetermined width L;
   a compression step of compressing, in a longitudinal direction of the tubular mesh body, the axial end portions that are expanded to be flared out when the principal body portion of the tubular mesh body is tightly fastened to the surface of the jig by the second wire strand, by pushing the axial end portions toward the middle portion of the tubular mesh body from opposing directions, via disks respectively disposed to be in surface contact with ends of the tubular mesh body, in the longitudinal direction of the tubular mesh body;
   a second fastening step of fastening the disks to the respective axial ends of the cylindrical mesh body, which are compressed and deformed through the compression step;
   a heat treatment step of performing heat treatment for shape memory, on the tubular mesh body resulting from the second fastening step so that a shape of the tubular mesh body, which is deformed through the second fastening step, is maintained; and
   a zig removal step of removing the zig from the tubular mesh body to finally produce the stent.

2. The method according to claim 1, wherein in the compression step at which the disks are pushed toward the axial middle portion of the tubular mesh body to approach each other until axial movements of the disks are stopped by the fixing pins arranged to demarcate the principal body portion of the tubular mesh body, each of the axial end portions of the tubular mesh body expands in a radial direction to increase a diameter thereof while being crimpled and multi-folded to form a compressed washer-shaped end, in which a part of the axial end portion forms a supporting surface and the remaining part forms a reinforced supportive rim provided at a circumferential periphery of the washer-shaped end and having a larger diameter than any other portion of the stent.

3. The method according to claim 2, wherein the number of folds in the reinforced supportive rim varies according to the width L of each of the axial end portions of the tubular mesh body, which is unwound by the second wire strand.

4. The method according to claim 2, wherein the washer-shaped end includes the supporting surface perpendicular to the tubular mesh body.

5. The method according to claim 2, wherein the washer-shaped end includes the supporting surface having an obtuse angle with respect to the tubular mesh body.

6. The method according to claim 2, wherein the washer-shaped end includes the supporting surface having an acute angle with respect to the tubular mesh body.

7. A method of manufacturing a stent with a reinforced supportive axial end, the method comprising:
   a stent preparation step of obtaining a stent having a tubular mesh body and a uniform diameter;
   a jig installation and pin arrangement step of fitting the stent on a jig having a smaller diameter than the stent and arranging fixing pins along a circumferential direction of the stent to demarcate a principal body portion of the tubular mesh body;
   a first fastening step of fastening the tubular mesh body to the jig by winding a first wire strand around the tubular mesh body while leaving both axial end portions, each having a predetermined width L from a corresponding end, of the tubular mesh body unwound;
   a compression step of compressing each of the axial end portions in an axial direction by pushing disks being in surface contact with the respective ends of the tubular mesh body toward an axial middle portion of the tubular mesh body, whereby each of the axial end portions, which deforms to be expanded in a flare-out form when the tubular mesh body which is a middle portion of the stent is wound by the second wire strand at the first fastening step;
   a second fastening step of fastening the disks to the respective axial ends of the cylindrical mesh body, using the second wire strand after the lateral movements of the respective disks toward the axial middle portion are stopped by the fixing pins;
   a heat treatment step of performing heat treatment for shape memory on the stent deformed through the second fastening step to maintain the deformed state of the stent; and
   a jig removal step of removing the jig to produce a medical stent as a final product.

8. The method according to claim 7, wherein in the compression step at which the disks are pushed toward the axial middle portion of the tubular mesh body to approach each other until axial movements of the disks are stopped by the fixing pins arranged to demarcate the principal body portion of the tubular mesh body, each of the axial end portions of the tubular mesh body expands in a radial direction to increase a diameter thereof while being crimpled and multi-folded to form a compressed washer-shaped end, in which a part of the axial end portion forms a supporting surface and the remaining part forms a reinforced supportive rim provided at a circumferential periphery of the washer-shaped end and having a larger diameter than any other portion of the stent.

9. The method according to claim 8, wherein the number of folds in the reinforced supportive rim varies according to the width L of each of the axial end portions of the tubular mesh body, which is unwound by the second wire strand.

10. The method according to claim 8, wherein the washer-shaped end includes the supporting surface perpendicular to the tubular mesh body.

11. The method according to claim 8, wherein the washer-shaped end includes the supporting surface having an obtuse angle with respect to the tubular mesh body.

12. The method according to claim 8, wherein the washer-shaped end includes the supporting surface having an acute angle with respect to the tubular mesh body.

\* \* \* \* \*